United States Patent [19]

Uneme et al.

[11] Patent Number: 5,726,338
[45] Date of Patent: Mar. 10, 1998

[54] PROCESS FOR PRODUCING ISOTHIOCYANATE DERIVATIVES

[75] Inventors: Hideki Uneme; Yasuo Kamiya, both of Tsukuba, Japan

[73] Assignee: Takeda Chemical Industries, Ltd., Osaka, Japan

[21] Appl. No.: 712,838

[22] Filed: Sep. 12, 1996

[30] Foreign Application Priority Data

Sep. 12, 1995 [JP] Japan .................. 7-233769

[51] Int. Cl.$^6$ .................. C07C 331/22
[52] U.S. Cl. .................. 558/17
[58] Field of Search .................. 558/17

[56] References Cited

U.S. PATENT DOCUMENTS 3,342,846  9/1967  Cometti et al. .................. 558/17
5,354,777  10/1994  Wachtler et al. .................. 558/17 X

FOREIGN PATENT DOCUMENTS 0 446 913  3/1991  European Pat. Off. .
6-256326  9/1994  Japan .

OTHER PUBLICATIONS

H.E. Armstrong et al., "Dixon: Halogen–Substituted Thiosinamines", Journal of the Chemical Society, 1901, vol. 79. (1901).
Berichte Der Deutschen Chemische Gesellschaft Zu Berlin, p. 188, vol. 5, (1872).

Primary Examiner—Michael G. Ambrose
Attorney, Agent, or Firm—Foley & Lardner

[57] ABSTRACT

A process for producing 2-halogenoallyl isothiocyanate [I] represented by the formula:

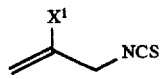

wherein $X^1$ is a halogen atom, is disclosed. The process comprises reacting a compound represented by the formula:

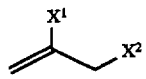

wherein $X^1$ is a halogen atom and $X^2$ is a leaving group, with a thiocyanate represented by the formula;

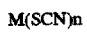

M(SCN)n wherein M is a metal or an ammonium group and n is a valence number of M, in the presence of water under heating. According to the process for producing of the present invention, 2-halogenoallyl isothiocyanata [I], which has an insecticidal effect as such and is useful as an intermediate for a medicine, an agricultural chemical and the like, can be produced on an industrially large scale in a good yield.

15 Claims, No Drawings

PROCESS FOR PRODUCING ISOTHIOCYANATE DERIVATIVES

[FIELD OF THE INVENTION]

The present invention relates to an improved industrial process for producing a 2-halogenoallyl isothiocyanate represented by the formula [I]

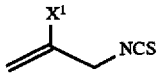

wherein $X^1$ is a halogen atom, which is useful as a pesticide having a nematocidal activity and as an intermediate for medicines, agricultural chemicals and the like.

[BACKGROUND OF THE INVENTION]

Processes for producing the 2-chloroallyl isothiocyanate were described in, for instance, Journal of the Chemical Society, 553,(1901), EP-A No. 446913 and Japanese Patent Application Laid Open No. 256326/1994. In those processes, ms shown in Schema 1 mentioned below, first 2,3-dichloro-1-propene and thiocyanate are reacted in an organic solvent having a relatively low boiling point such as ethanol, acetonitrile and the like, the solvent and inorganic substances are removed, and then the reaction mixture is re-heated at about 110° to 140° C. in the absence of a solvent or in a higher boiling organic solvent such as toluene, xylene and the like to give 2-chloroallyl isothiocyanate. These procedures promote the conversion of 2-chloroallyl thiocyanate (II), an intermediate accumulated in the first half of the reaction, to the desired 2-chloroallyl isothiocyanate by re-heating at a higher temperature.

Schema 1

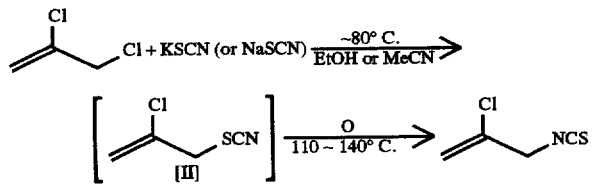

The 2-halogenoallyl isothiocyanate [I] is irritating to the eyes and skin, and therefore, it has been desired to develop an industrial process for production of 2-halogenoallyl isothiocyanate [I], which is simpler and more convenient as well as safer in the reaction procedures and gives a better yield.

In investigating the problem discussed above, the present inventors found that by reacting 2,3-dihalogeno-1-propene, such as 2,3-dichloro-1-propene, with thiocyanate represented by the formula

 [IV]

wherein M is a metal or an ammonium group and n is a valence number of M (optionally called compound [IV] hereinbelow) in the presence of water under heating, the reaction proceeds smoothly to the stage of rearrangement reaction and to give the desired 2-halogenoallyl isothiocyanate such as 2-chloroallyl isothiocyanate in a high yield in one-step reaction. The reaction process is shown in Schema 2.

Schema 2

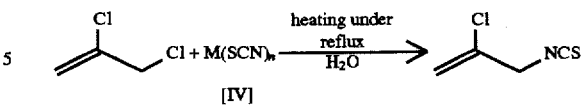

wherein the symbol is the same as defined above.

The starting material of the above-mentioned reaction, 2,3-dihalogeno-1-propene is insoluble in water and the compound [IV] is soluble in water. Therefore it would be expected that its reactivity of 2,3-dihalogeno-1-propene with the compound [IV] would be lower in the presence of water than in the presence of an organic solvent. However, contrary to that expectation, the reaction of 2,3-dihalogeno-1-propene with the compound [IV] in the presence of water under heating proceeds rapidly.

The process for production mentioned above has advantages over the prior art in the reaction procedure. For example, the desired 2-halogenoallyl isothiocyanate can be obtained in one-step reaction. Also, by the simple workup procedure, the removal of the excess amount of thiocyanate and the by-product salt (MCln, the respective symbols are the same as those defined above) can be effectively removed by a phase separation after the reaction.

[SUMMARY OF THE INVENTION]

The present invention relates to:

(1) A process for producing a compound of the formula:

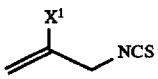 [I]

wherein $X^1$ is a halogen atom, which comprises reacting a compound of the formula:

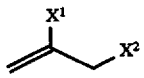 [III]

wherein $X^1$ is as defined above and $X^2$ is a leaving group, with a thiocyanate of the formula:

M(SCN)n [IV]

wherein M is a metal or an ammonium group and n is a valence number of M in the presence of water under heating.

(2) A process according to (1), wherein $X^2$ is a halogen atom.

(3) A process according to (1), wherein $X^1$ and $X^2$ are both chlorine.

(4) A process according to (1), wherein M is an alkali metal or $NH_4^+$.

(5) A process according to (1), wherein the reaction is conducted in the range of from or about 90° to or about 150° C.

(6) A process according to (1), wherein the reaction is conducted at or about 100° C.

(7) A process for producing a compound of the formula [I]:

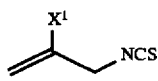

[I]

wherein $X^1$ is as defined in (1), which comprises reacting a compound of the formula:

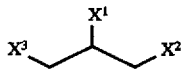

wherein $X^1$ and $X^2$ are as defined in (1) and $X^3$ is a leaving group with a base, to produce the compound [III], and further reacting the resultant compound [III] with the compound [IV] in the presence of water under heating.

(8) Use of the compound [III] for the production of the compound [I] which comprises reacting the compound [III] with the compound [IV] in the presence of water under heating.

[DETAILED DESCRIPTION OF THE INVENTION]

The examples of halogen atoms defined by $X^1$ in the above formulas include fluorine, chlorine, bromine and iodine. Among them, fluorine, chlorine and bromine are preferable and chlorine is particularly preferable.

As the leaving group defined by $X^2$ in the above formulas is used any group which is removed from the compound [III] when the compound [III] is reacted with the compound [IV]. The examples of leaving groups defined by $X^2$ include halogen e.g. fluorine, chlorine, bromine, iodine, etc., $C_{1-11}$ acyloxy groups which may be substituted with 1–5 halogens, etc., e.g. formyloxy, acetyloxy, trifluoroacetyloxy, benzoyloxy, etc., $C_{1-4}$ alkylsulfonyloxy groups which may be substituted with 1–5 halogens, etc., e.g. methanesulfonyloxy, ethanesulfonyloxy, butanesulfonyloxy, trifluoromethanesulfonyloxy, etc., $C_{6-10}$ arylsulfonyloxy groups which may be substituted with 1–5 lower alkyls ($C_{1-6}$ alkyl such as methyl, ethyl, etc.) and/or halogens, etc., e.g. benzenesulfonyloxy, p-toluenesulfonyloxy, p-bromobenzenesulfonyloxy, mesitylenesulfonyloxy, etc. As $X_2$, a halogen atom is preferable and chlorine atom is particularly preferable. As the compound [III], 2,3-dichloro-1-propene is particularly preferable.

As the metal defined by M in the above formula any metal which can form a salt with thiocyanate anion can be used. Among them, for example, mono-valent or di-valent metal is preferably employed. As concrete examples are used, for example, an alkali metal such as sodium, potassium, etc., an alkaline earth metal such as magnesium, calcium, etc.

As the examples of the ammonium group defined by M in the above formula, there may be mentioned, among them, $NH_4^+$ and $(C_{1-6} \text{alkyl})_4 N^+$ wherein $C_{1-6}$ alkyl group is, for example, methyl, ethyl, propyl, isopropyl, buryl, t-butyl, pentyl, hexyl, etc.

As M, are used preferably alkali metals, alkaline earth metals and ammonium groups, more preferably alkali metals and $NH_4^+$. It is preferable that that the compound [IV] is substantially water soluble. It is preferable that at least about 5 g of the compound [IV] can be dissolved in 100 ml of water at room temperature. The particularly preferable examples of the compound [IV] include, for example, sodium thiocyanate, potassium thiocyanate and ammonium thiocyanate.

"n" stands for an atomic valence number of the metal ion or ammonium ion defined by M, and is, in general, an integer of 1 to 4. When M is sodium, potassium and $NH_4^+$, n is 1.

The present process for production can be carried out according to the reaction conditions, for example, as mentioned below by reacting the compound [III] with the compound [IV] in the presence of water under heating that components (III) and (IV) can be reacted in any desired proportions, at any temperature, pressures, and times, and in the presence of any amount of water or optional solvent, so long as the desired compound (I) is obtained. Examples of useful conditions follow:

The compound [III] is employed in a proportion of about 0.5–5 equivalents, preferably about 0.8–1.5 equivalents relative to the compound [IV], but may be used in a large excess amount unless the reaction is hindered.

The reaction is usually carried out in water. Water is used in a proportion of about 0.1–20 times by weight, preferably about 0.5–50 times by weight relative to the compound [III]. An organic solvent is not needed in the present invention. An organic solvent may be added thereto if the reaction is not hindered. As the organic solvent are used, e.g. aromatic hydrocarbons such as benzene, toluene, xylene, etc., e.g. halogenated hydrocarbons such as dichloromethane, chloroform, 1,2-dichloroethane, carbon tetrachloride, etc., e.g. saturated hydrocarbons such as hexane, butane, cyclohexane, etc., e.g. ethers such as diethyl ether, tetrahydrofuran, dioxane, etc., e.g. ketches such as acetone, methyl ethyl ketone, etc., e.g. nitriles such as acetonitrile, propionitrile, etc., e.g. sulfoxides such as dimethyl sulfoxide, etc., e.g. acid amides such as N,N-dimethylformamide, N,N-dimethylacetamide, etc., e.g. esters such as ethyl acetate, butyl acetate, etc., e.g. alcohols such as methanol, ethanol, propanol, isopropanol, etc. These solvents may be used either alone or, as required, in combination of two or more in an appropriate ratio, for example, a ratio of about 1:1 to about 1:10.

The amount of the organic solvent to be added is usually about 0.3 volume relative to i volume of water in the neighborhood of 108° C. or less, preferably about 0.01 to 0.3 volume relative to 1 volume of water. The reaction mixture usually forms two layers, and therefore, the reaction may be carried out in the presence of a phase transfer catalyst, e.g., a quaternary ammonium salt such as triethylbenzylammonium chloride, tri-n-octylmethylammonium chloride, trimethyldecylammonium chloride, tetramethylammonium bromide and cetylpyridinium bromide, a crown ether and the like. When the reaction temperature does not rise to about 100° C. after addition of the organic solvent the rearrangement reaction proceeds slowly and, in some cases, does not do so at all. In such cases, the solvent may be distilled off until the reaction temperature goes up beyond about 100° C. or the reaction temperature can be raised forcibly by the use of a pressure-resistant reaction apparatus and the like.

The reaction temperature is preferably in the range of from or about 90° to or about 150° C., more preferably is the range of from or about 90° to or about 110° C., most preferably at or about 100° C., i.e. the range of from or about 95° to or about 105° C. It is to be understood that these temperature ranges can vary according to, e.g. atmospheric pressure, solute concentration and type, etc.

The reaction per se of the compound [III] with the compound [IV] proceeds even below 90° C. in most cases, but the rearrangement reaction to the compound [I] may not always be complete without additional heating. Therefore, the reaction may be first carried out in a temperature ranging from room temperature to about 90° C., and then the reaction mixture may be heated at the aforementioned temperature to promote the rearrangment reaction, if necessary.

The reaction can usually be carried out under a pressure ranging from normal atmospheric pressure to 10 atmospheric pressure and preferably under a normal atmospheric pressure.

When the reaction is carried out by using 2,3-dichloro-1-propene as the compound [III] and water as the solvent under a normal atmospheric pressure, an azeotropic refluxing starts from about 80° C. However, as the reaction proceeds the refluxing temperature goes up gradually, and finally, in most cases, rises beyond 100° C.

Reaction time is usually in the range of about 30 minutes to 50 hours, preferably about 2 to 10 hours.

The reaction is usually carried out in the room atmosphere or in the atmosphere of an inert gas (e.g. nitrogen gas, argon gas, etc..) and preferably in the inert gas (e.g. nitrogen gas, argon gas, etc..).

The 2-halogenoallyl isothiocyanate [I] thus obtained can be purified according to known methods. As the purification methods, there may be mentioned concentration, concentration under reduced pressure, distillation, fractional distillation, solvent extraction, pH change, solvent change, chromatography and the like. When only water is used as a solvent, aftertreament procedure is particularly simple and convenient since the excess amount of thiocyanate [IV] and the inorganic salt as the by-product are usually soluble in the aqueous layer.

The starting material 1-propene derivative [III] in the present process is commercially available or can be prepared by the reaction of the propane derivative [V] with a base.

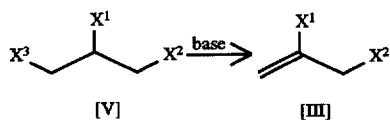

wherein $X^3$ is a leaving group, and other symbols are the same as defined above.

As the leaving group defined by $X^3$ are used similar ones to those defined by $X^2$. The examples of $X^3$ are preferably halogen atoms and, among them, chlorine is particularly preferable.

As the base is used, for example, an inorganic base such as alkali metal hydrogen carbonate (e.g. sodium hydrogen carbonate, potassium hydrogen carbonate, etc.), alkali metal carbonate (e.g. sodium carbonate, potassium carbonate, etc.), alkali metal hydroxide (e.g. sodium hydroxide, potassium hydroxide, etc.), alkaline earth metal hydroxide (e.g. calcium hydroxide, etc.), alkyl lithium (e.g. butyllithium etc.), aryl lithium (e.g. phenyllithium etc.), alkali metal amide (e.g. sodium amide, lithium diisopropylamide, etc.), alkali metal hydride (e.g. sodium hydride, potassium hydride, etc.), alkali metal alkoxide (e.g. sodium methoxide, sodium ethoxide, etc.), alkali metal (e.g. metallic sodium, metallic potassium, etc.) and the like, an organic base such as triethylamine, tributylamine, N,N-dimethylaniline, pyridine, picoline, lutidine, collidine, 5-ethyl-2-methylpyridine, 4-(dimethylamino)pyridine, 1,8-diazabicyclo[5.4.0]undec-7-ene (called DBU for short hereinbelow) and the like. A particularly preferable base is sodium hydroxide.

The base is used in an amount of about 0.8–5 equivalents, preferably about 1–1.5 equivalents relative to the compound [V]. An excess amount may also be used if the reaction is not hindered. The reaction is usually carried out in the organic solvents or water or the mixture thereof as described in the process for production of the present invention. In the case where the reaction mixture is not in homogeneous phase, a phase transfer catalyst may also be employed as stated above.

The reaction temperature is usually in the range of 0°–200° C., preferably 50°–150° C. The reaction time is usually in the range of about 10 minutes to 50 hours, preferably about 30 minutes to 6 hours. The particularly preferred solvent is water and, in such a case, is used a phase transfer catalyst, for example, such as a quaternary ammonium salt (e.g. benzyltriethylammonium chloride, trioctylmethylammonium chloride, etc.) in a catalytic amount (about 0.001–0.2 equivalent on the basis of the compound [V]). When 2,3-dichloro-1-propene is used, the methods described in, for example, Synthesis 1982, 494 and Japanese Patent Application Laid Open No. 5037/1988 can be employed.

The compound [III] after being prepared, for example, by the process mentioned above, can be subjected to the reaction with thiocyanate [IV] without isolation and/or purification. Of course, commercially available compound [III] or isolated and purified compound [III] may be used as well. Compound [IV] is usually commercially available. Compound [V] is also commercially available or is produced by the known methods (J. Am. Chem Soc., 3432, 61 (1939) and Japanese Patent Application Laid Open No. 68432/1986) or by similar methods thereto.

[EXAMPLES]

The invention will be described in more detail below with Examples and Reference Examples. However, the invention is not intended to be limited to these examples.

The proton NMR spectra ($^1$H NMR) in the examples were measured on BURCAR AC-200P type spectrometer using tetramethylsilane as the internal standard and being indicated in terms of all δ value in ppm.

Abbreviations in the examples have the following meanings.

dd: doublet of doublet, dt: doublet of triplet,

J: coupling constant, Hz: herz, $CDCl_3$:deutero-chloroform. Room temperature means a temperature of ca. 15°–25° C.

Example 1

A mixture of 2,3-dichloro-1-propene (1.12 kg, 10.1 mol), potassium thiocyanate (0.99 kg, 10.1 mol) and water (2.02 L) was heated gradually with stirring under a nitrogen gas stream. The reaction mixture began to reflux around 80° C. The refluxing temperature was raised gradually and after 5 hours reached 104° C. After heating under reflux for 6 hours in total, the reaction mixture was cooled to room temperature and the organic layer was separated from the aqueous layer. The organic layer was washed with water (1.00 L) and dried over anhydrous magnesium sulfate to give 1.27 kg of crude 2-chloroallyl isothiocyanate.

Boiling point: 64°–68° C./10–13 mmHg, $^1$H NMR($CDCl_3$) δ=4.25(2H, dd, J=1.3, 1.0 Hz), 5.45 (1H, dt, J=2.3, 1.0 Hz), 5.55(1H, dr, J=2.3, 1.3 Hz).

Example 2

A mixture of 2,3-dichloro-1-propene(1.07 kg, 9.36 mol), potassium thiocyanate (0.91 kg, 9.32 mol) and water (1.86 L) was heated gradually with stirring under a nitrogen gas stream. The reaction mixture began to reflux around 75° C. The refluxing temperature went up gradually, and reached 108° C. after 4 hours. After heating under reflux for 8 hours in total the reaction mixture was cooled to room temperature and the organic layer was separated from the aqueous layer. The aqueous layer was extracted with hexane (100 ml). The extract was put together with the organic layer, washed with water (1.00 L) twice and dried over anhydrous magnesium sulfate. Hexane was distilled off and the residue was heated at 120° C. for 2 hours and then cooled, hexane was added (8.00 L) and the mixture stirred vigorously for about 1 hour. The resulting suspension was kept standing at room temperature for 2 hours and insolubles were removed by decantation. The hexane solution was concentrated under reduced pressure to give crude 2-chloroallyl isothiocyanate (1.1 kg). NMR spectrum was confirmed to be identical with that of Example 1.

Example 3

A mixture of 2,3-dichloro-1-propene (578 g, 5.05 mol), sodium thiocyanate (4.09 g, 5.00 mol) and water (1.00 L) was heated gradually with stirring under a nitrogen gas stream. The reaction mixture began to reflux around 75° C. The refluxing temperature was raised gradually and reached 104° C. after 4 hours. After heating under reflux, for 5 hours in total, the resulting mixture was cooled to room temperature and the organic layer was separated from the aqueous layer. The organic layer was washed with water (500 ml) twice, and dried over anhydrous magnesium sulfate to give crude 2-chloroallyl isothiocyanate (580 g). NMR spectrum was confirmed to be identical with that of Example 1.

Example 4

A mixture of 2,3-dichloro-1-propene (45.8 g, 0.40 mol), ammonium thiocyanate (36.9 g, 0.48 mol) and water (90 ml) was heated gradually with stirring. The reaction mixture began to reflux around 83° C. The refluxing temperature went up gradually and reached 103° C. After 5 hour heating in total under reflux, the reaction mixture was cooled to room temperature and the organic layer was separated from the aqueous layer. The aqueous layer was extracted with chloroform (100 ml). The chloroform layer was put together with the organic layer and dried over anhydrous magnesium sulfate. The solution was concentrated under reduced pressure to give crude 2-chloroallyl isothiocyanate (46.8 g). NMR spectrum was confirmed to be identical with that of Example 1.

Example 5

Into a solution of sodium hydroxide (22.9 g, 0.55 mol) in 88 ml of water, trioctylmethylammonium chloride (2.00 g, 5.00 m mol) and 1,2,3-trichloropropane (73.7 g, 0.50 mol) were added and the mixture was heated under reflux for 3 hours. The reaction mixture was cooled to about 50° C. and the organic layer was separated from the aqueous layer and washed with water. The organic layer was added into a mixture of 100 ml of water and potassium thiocyanate (55.7 g, 0.55 mol), and the mixture was heated under reflux at a temperature ranging from 90° to 104° C. under a nitrogen gas stream for 3 hours. The resultant mixture was cooled around room temperature and the organic layer was separated from the aqueous layer. The aqueous layer was extracted with hexane (50 ml). The hexane layer was put together with the separated organic layer and dried over anhydrous magnesium sulfate. Hexane was distilled off from the organic layer to give crude 2-chloroally isothiocyanate (61.0 g). NMR spectrum was confirmed to be identical with that of Example 1.

Reference Example (Reaction in toluene)

A mixture of 2,3-dichloro-1-propene (11.4 g, 0.1 mol), potassium thiocyanate (10.3 g, 0.11 mol) and toluene (45 ml) was heated under reflux for 2 hours, but almost no reaction occurred.

According to the process for production of the present invention, 2-halogenoallyl isothiocyanate [I], which has an nematocide effect as such and is useful as an intermediate for a medicine and pesticide and the like, can be produced on an industrially large scale in a good yield in one step reaction. Also, by the simple workup procedure, the removal of the excess amount of thiocyanate and the by-product salt can be effectively removed by a phase separation after the reaction.

Priority application number 233769 filed Sep. 12, 1995, including the specification, claims, and abstract, is hereby incorporated by reference in its entirety.

We claim:

1. A process for producing a compound of the formula:

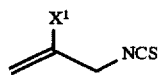   (I)

wherein $X^1$ is a halogen atom, which comprises reacting a compound of the formula:

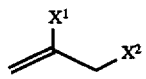   (III)

wherein $X^1$ is as defined above and $X^2$ is a leaving group, with a thiocyanate of the formula:

   (IV)

wherein M is a metal or an ammonium group and n is the valence number of M in the presence of water at a temperature in a range from about 90° to about 150° C.

2. The process according to claim 1, wherein $X^2$ is a halogen atom.

3. The process according to claim 1, wherein $X^1$ and $X^2$ are both chlorine.

4. The process according to claim 1, wherein M is an alkali metal or $NH_4^+$.

5. The process according to claim 1, wherein the reaction is conducted at about 100° C.

6. The process according to claim 1, wherein the reaction takes place in the absence of organic solvent.

7. The A process according to claim 1, wherein the water is used in the reaction in a proportion of about 0.1 to 20 times by weight relative to the weight of compound (III).

8. A process for producing a compound of the formula:

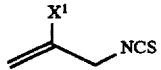   (I)

wherein $X^1$ is a halogen atom, which comprises reacting a compound of the formula:

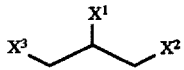   (V)

wherein $X^1$ is as defined above and $X^2$ and $X^3$ are independently a leaving group, with a base, to produce a compound of the formula:

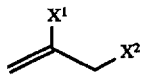   (III)

wherein $X^1$ and $X^2$ are as defined above, and further reacting the resultant compound of the formula (III) with a compound of the formula:

M(SCN)n  (IV)

wherein M is a metal or an ammonium group and n is a valence number of M in the presence of water under heating.

9. The process according to claim 8, wherein $X^2$ is a halogen atom.

10. The process according to claim 8, wherein $X^1$ and $X^2$ are both chlorine.

11. The process according to claim 8, wherein M is an alkali metal or $NH_4^+$.

12. The process according to claim 8, wherein the reaction of compound (III) with compound (IV) is conducted in a range from about 90° to about 150° C.

13. The process according to claim 8, wherein the reaction of compound (III) with compound (IV) is conducted at a temperature of about 100° C.

14. A process according to claim 8, wherein the reaction of compound (V) with the base takes place in water.

15. A process for producing a compound of the formula:

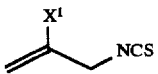  (I)

wherein $X^1$ is a halogen atom, which comprises reacting a compound of the formula:

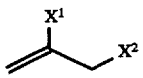  (III)

wherein $X^1$ is as defined above and $X^2$ is a leaving group, with a thiocyanate of the formula:

M(SCN)n  (IV)

wherein M is a metal or an ammonium group and n is a valence number of M in the presence of water and in the absence of an organic solvent under heating.

* * * * *